United States Patent [19]
Melling

[11] Patent Number: 5,923,808
[45] Date of Patent: Jul. 13, 1999

[54] MID-INFRARED FIBER-OPTIC SPECTROSCOPIC PROBE FOR USE AT ELEVATED TEMPERATURES

[76] Inventor: Peter J. Melling, 512 Leadmine Rd., Sturbridge, Mass. 01566

[21] Appl. No.: 08/880,691

[22] Filed: Jun. 23, 1997

[51] Int. Cl.[6] .................................................. G02B 6/36
[52] U.S. Cl. ............................ 385/139; 385/12; 385/902
[58] Field of Search ....................... 250/227.17, 227.18, 250/227.19; 385/12–13, 139, 31, 33–39, 47–50, 147, 902

[56] References Cited

U.S. PATENT DOCUMENTS

| | | | |
|---|---|---|---|
| 4,039,845 | 8/1977 | Oberhänsli et al. ................... | 385/12 X |
| 4,468,771 | 8/1984 | Zhukov et al. ........................ | 385/12 X |
| 4,909,588 | 3/1990 | Harner et al. ......................... | 385/12 |
| 5,185,834 | 2/1993 | Day et al. ............................. | 385/47 |
| 5,351,322 | 9/1994 | VonBargen ........................... | 385/12 |
| 5,652,810 | 7/1997 | Tipton et al. ......................... | 385/13 X |

*Primary Examiner*—John D. Lee

[57] ABSTRACT

A mid-infrared spectroscopic probe attached to a fiber-optic cable comprises an optically transparent, heat-insulating crystal which is placed between the ATR crystal and the end of the fiber-optic cable so as to provide optical coupling from the cable to the ATR crystal while protecting the fiber-optic assembly inside the cable from excessive heat when the probe is used in high-temperature sample streams. The ATR crystal is tapered outwards towards the sampling end to ensure that pressure from the sample stream, e.g., in a plastics extruder, does not displace the crystal, but rather forces it into tighter contact with the seal in the probe head.

10 Claims, 5 Drawing Sheets

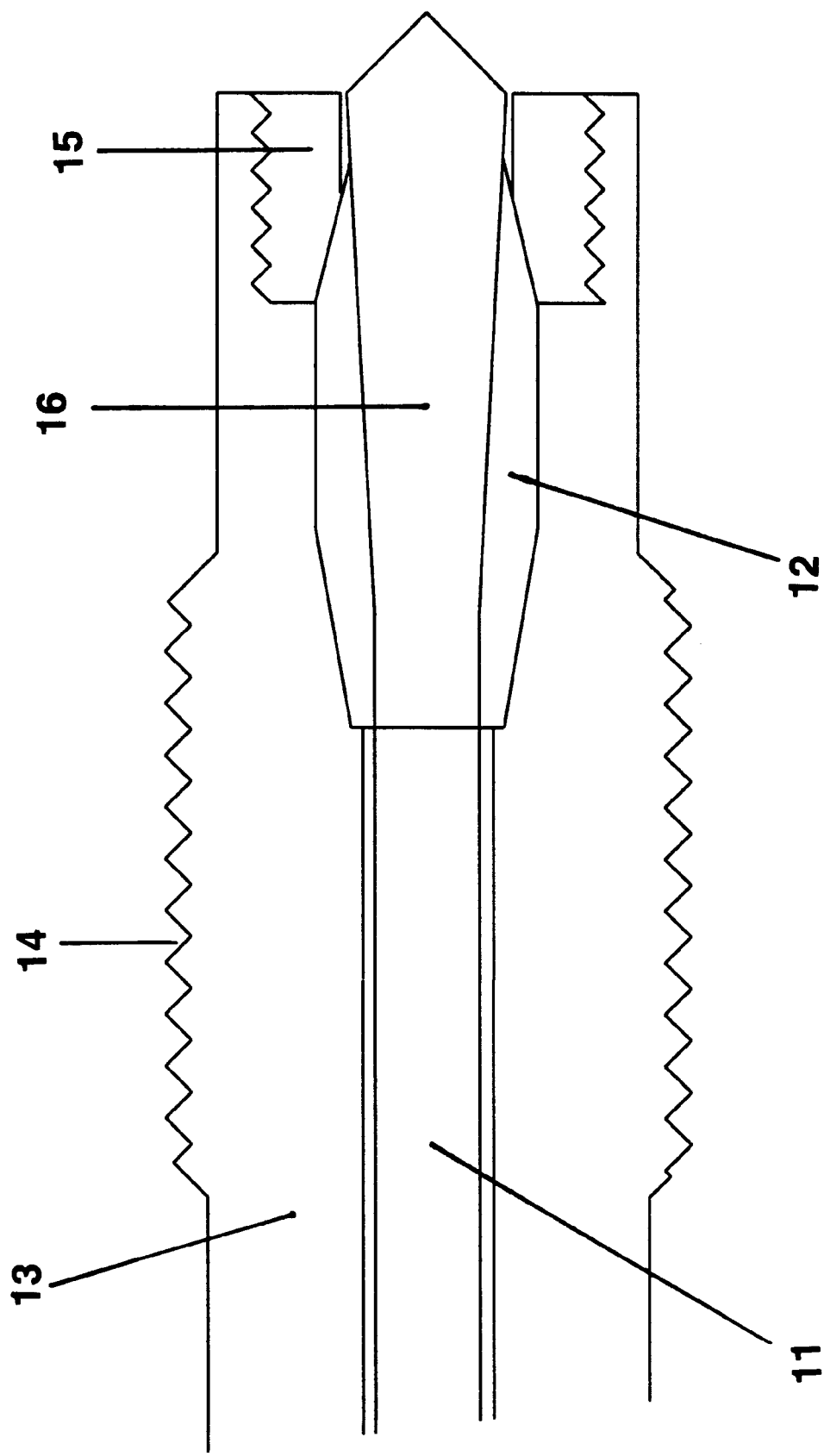

MID-INFRARED FIBER-OPTIC SPECTROSCOPIC PROBE FOR USE AT ELEVATED TEMPERATURES

BACKGROUND OF THE INVENTION

1. Field of the Invention

The present invention relates to accessories used in conjunction with spectrophotometers and spectrometers, more particularly with Fourier Transform Infrared (FTIR) spectrometers. These accessories use infrared-transmitting optical fibers to enable spectral analysis of samples remote from the body of the FTIR spectrometer and, in particular, are adaptable for use in monitoring chemical reactions and chemical manufacturing processes which may be proceeding at elevated temperatures and/or pressures.

2. Prior Art

The use of optical fibers and, in particular, optical fiber cables, to enable collection of FTIR spectra directly from chemical reactors or other sites without the need to remove samples and transfer them to a compartment inside the spectrometer is well known. For example, a fiber-optic probe has been used to obtain spectra from an electrochemical reactor (Shaw and Geiger, Organometallics, 1996, 15; 13–15) in which air-sensitive species and transient intermediates were identified in situ, and kinetic data were obtained in a convenient manner using a standard electrochemical reactor, without perturbing the course of the reaction or admitting air to the reactor. When this method is used in the mid-IR region of the spectrum (approximately 700–5000 $cm^{-1}$), it is often necessary to use optical fibers made of materials, typically chalcogenide or fluoride glasses, that are liable to undergo phase transformations such as melting or crystallization at comparatively low temperatures. Means exist to provide some protection for the optical fibers (which typically do not directly contact the medium under examination) by, for example, adding a cooling jacket which circulates water around the outer casing of the optical fiber cable (see copending patent application Ser. No. 08/380,078). This means is effective for cases where the temperature is elevated but still comparatively modest (for example, up to approx. 100 deg. C.), and in circumstances where there is no practical objection, such as a safety hazard, to the use of water close to the reactor or other vessel. However, in cases where temperatures are considerably higher—up to 400 deg. C. for example—the degree of cooling that can be provided by the water jacket is inadequate, and it may be impractical or undesirable to use water in close proximity to the reactor or vessel under examination.

A particular situation where remote spectroscopic monitoring in real time can be highly advantageous is in the field of plastics or polymer extrusion. Plastics are extruded in a fluid, but usually somewhat viscous, state at temperatures ranging up to well above 300 deg. C. Chemical reactions, including polymerization reactions and other changes, can take place during extrusion inside the extruder. Other parameters, such as the volumetric distribution of particulates such as fillers, colorants, antioxidants, stabilizers, etc. or the homogeneity of polymer blends or alloys, may also be subject to change or variation under the conditions of temperature, pressure, flow, etc. that prevail inside the extruder. Because of the importance of monitoring all of the various quality- and composition-related parameters in extruded materials, considerable resources are often expended to provide quality control laboratory facilities; however, the process feedback from such laboratories is often slow, making process control based on laboratory results difficult and compromising the real-time nature of the results. A better approach is to devise an on-line or in-line method for monitoring the material in the extruder.

Several attempts have been made to use near infrared (NIR) spectroscopy for monitoring of polymer processes in the extruder. For example, an anonymous Research Disclosure (RD 29959, March 1989) describes the use of a NIR probe based on a sapphire or quartz rod to obtain real-time, in-line NIR data from polymer melts; the probe can be designed to fit into a standard well, such as a Dynisco Pressure Well, in an extruder. Others, including McPeters and Williams (Process Control and Quality, 1992, 3, 75–83) and Khettry and Hansen (Polymer Engineering and Science, 1996, 36, 1232–1243) have used fiber-optic cables based on silica fibers to couple NIR spectrometers to probes for in-line monitoring of polymer melts in extruders. All of these NIR methods have a number of serious, inherent disadvantages. Because of the low extinction coefficients (i.e. low molecular absorbance) exhibited by NIR radiation, relatively long path lengths are required; this means that transmission or transflectance techniques have to be used, leading to the use of complex sampling elements that interfere with the flow inside the extruder; this is in contrast to the convenience of evanescent wave techniques such as attenuated total reflectance (ATR), which can be used successfully in the mid-IR region of the spectrum where higher extinction coefficients prevail. Another problem arises from the nature of NIR spectra, which are characterized by weak bands which tend to be broad and overlapping, and by scattering of the NIR signal in multiphase systems such as polymer blends or polymers containing fillers. As a result, spectral interpretation in the NIR is almost always based on mathematical analysis by the partial least squares (PLS) method, which requires the generation of extensive calibration sets of spectra based on predetermined mixtures of standard compounds. The mid-IR region of the spectrum exhibits higher extinction coefficients and thus shorter path lengths can be used to obtain usable spectra; this enables the use of the ATR method rather than transmission or reflectance. Furthermore, mid-IR spectra comprise sharper better separated peaks than those in the NIR, obviating the need for PLS methods of interpretation, with the accompanying laborious calibration, in most cases. However, previous attempts to use mid-IR spectroscopy as a tool for monitoring chemical events inside an extruder (see, for example, H. L. McPeters, Anal Chim. Acta, 238 (1990), 83) have utilized complicated methods of sample handling by creating a side stream of material from the extruder into a short path-length transmission sample cell. While this method has the advantages over NIR methods that the spectra comprise strong peaks and contain a wealth of chemical information, and that they are in most cases able to be interpreted without the use of mathematical methods such as PLS, the removal of a side stream requires mechanical adaptation of the extruder, perturbs the flow in the extruder and compromises the real-time nature of the experiment, which is best described as on-line rather than in-line. The best solution to the above problems would be to use a fiber-optic probe operating in the mid-IR, and such devices are well known (see, for example, U.S. Pat. No. 5,170,056). This would permit true in-line monitoring of the polymer melt without the need for PLS interpretation. However, since fiber-optics capable of transmitting in the mid-IR are frequently made from materials such as heavy metal fluoride glasses or chalcogenide glasses which are subject to optical deterioration at temperatures close to or above 100 deg. C., their use in proximity to a plastics extruder or any other apparatus heated above about 200 deg C. has been a practical impossibility until the advent of the present invention.

SUMMARY OF THE INVENTION

It is an object of the present invention to provide a means for obtaining mid-IR spectra from samples, and in environments, that are heated to temperatures in excess of 300 deg C. and pressurized to pressures of 1500 psi or greater, and to do so in real time with minimum perturbation of the reaction and/or flow conditions prevailing in the sample environment.

In a particular embodiment, the invention is directed to a probe in which the end of a fiber-optic cable capable of transmitting in the mid-IR region of the spectrum is optically coupled to a sampling element such as an attenuated total reflectance (ATR) crystal or a transmission or reflectance cell by means of a heat-insulating material which is capable of optical transmission in the mid-IR range.

BRIEF DESCRIPTION OF THE DRAWINGS

FIG. 2 is an expanded view of the end of the high-temperature ATR sampling element.

Figure 1:
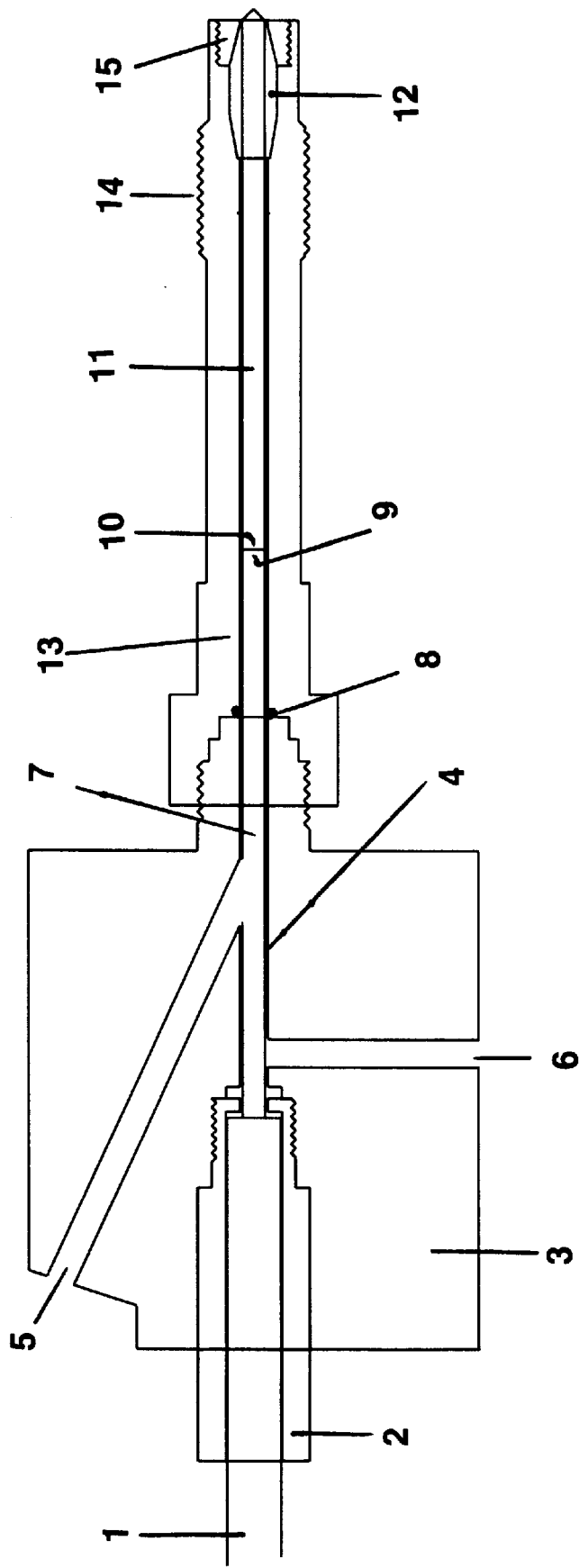
FIG. 1 is an illustration of a high-temperature ATR sampling element suitable for use with a plastics extruder.

| Reference Numerals in Drawings | |
|---|---|
| 1 Optical fiber bundle | 2 Screw-threaded insert |
| 3 Probe body | 4 Crystal conduit |
| 5 Inlet for cooling gas | 6 Outlet for cooling gas |
| 7 Heat-insulating crystal | 8 Sealing gasket |
| 9 Flat crystal end | 10 Flat crystal end |
| 11 Sampling ATR crystal | 12 Seal |
| 13 Sampling element body | 14 Threaded fitting |
| 15 End plug | 16 Flared crystal end |
| 17 Relay optic | 18 Flat end surface |
| 19 Ingress hole | 20 Mirror surface |
| 21 Transmission head | |

DETAILED DESCRIPTION OF THE PREFERRED EMBODIMENTS

A sketch of one preferred embodiment of the probe is shown in FIG. 1. The fiberoptic cable (1) comprises optical fibers which transmit in the mid-IR, made from materials such as arsenic-selenium-tellurium (AsSeTe) glass or a polycrystalline silver halide, for example. The cable (1) is attached to the probe head (3) by means of a screw-threaded insert (2). The probe head, the insert, and other structural parts are preferably made of stainless steel, although other materials such as Hastalloy may be used if the environment in which the probe will be used is particularly corrosive. The probe head is provided with a crystal conduit (4) and with an inlet (5) and an outlet (6) for cooling gas. The screw-threaded insert (2) is designed to center the fiber-optic cable with respect to the crystal conduit inside which an optically transmissive, heat-insulating crystal (7) is positioned; the crystal is preferably made from zinc selenide, zinc sulfide, or arsenic-germanium-selenium-tellurium (AMTIR) glass, but any material may be used which has appropriate heat-insulating and optically transmitting properties. A sealing gasket (8) is provided at the interface between the screw-threaded probe body and the probe head (12), which encloses the sampling ATR crystal (11) and centers it with respect to the heat-insulating crystal (7). Good optical contact between the ATR crystal and the heat-insulating crystal is ensured by providing both crystals with flat ends (9,10) which abut each other directly when the probe is fully assembled. The end of the sampling element distant from the fiber-optic cable, and adjacent to the sample environment, is held in place by an end plug (15) and is provided with a seal (12), preferably made from a soft metal such as copper or gold or from a material such as graphite-filled poly(tetrafluoroethylene) [PTFE], which retains the ATR crystal in position and prevents intrusion of material from the sample environment into the probe body. The sampling element may also be provided with a screw thread (14) and a sealing surface which is sized so as to fit into a suitable well in the reactor or extruder containing the sample under examination, such as the commonly used Dynisco type of fitting.

FIG. 2 shows an expanded view of the end of the sampling element used in one preferred embodiment of the invention. In cases where the extruder or reactor into which the sampling element will be inserted is pressurized, it is preferable to use an ATR crystal, or other sampling element, that is tapered or flared outwards (16) towards the end that is in contact with the sample. The taper or flare may be approximately 0.5 deg., and it provides for improved contact and sealing between the ATR crystal and the seal (12) when pressure from inside the extruder forces the ATR crystal into the probe head.

Figure 3A:
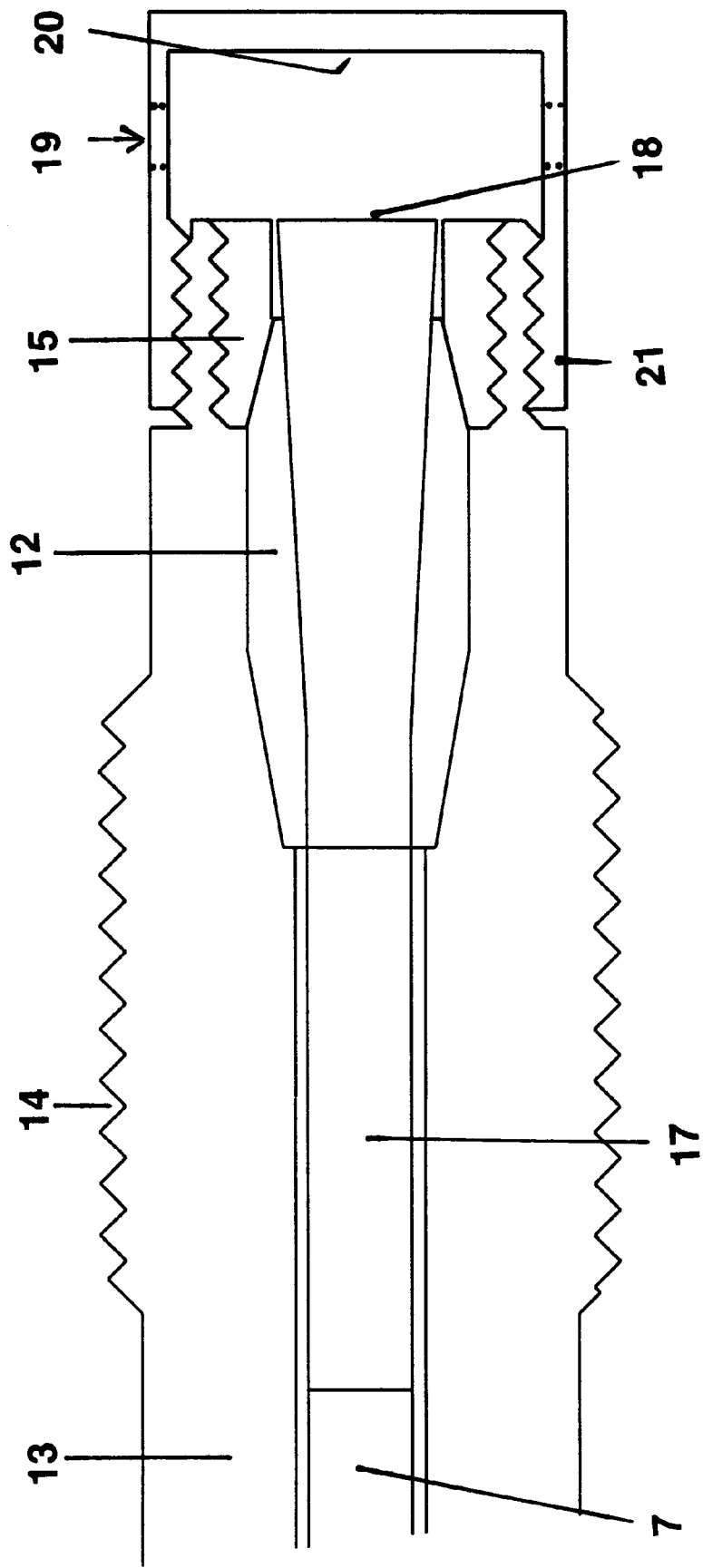
FIG. 3A is an expanded view of the end of the high-temperature transmission sampling element.

FIG. 3A shows an expanded view of one embodiment of a transmission sampling element. In this embodiment, a relay optic (17), which is preferably made from a material such as zinc selenide or zinc sulfide and which has a flat end (18) positioned proximate to the sample, is placed next to the optically transmissive, heat-insulating member (7). A transmission head (21) is attached to the end of the sampling element by means of a screw thread. The transmission head comprises ingress holes (19) which admit the fluid sample to the head, and a mirror surface (20) directly opposite the end of the relay optic. In use, the relay optic serves to transmit the IR signal through the sample to the mirror surface, from which it is reflected back to the end of the relay optic.

Figure 3B:
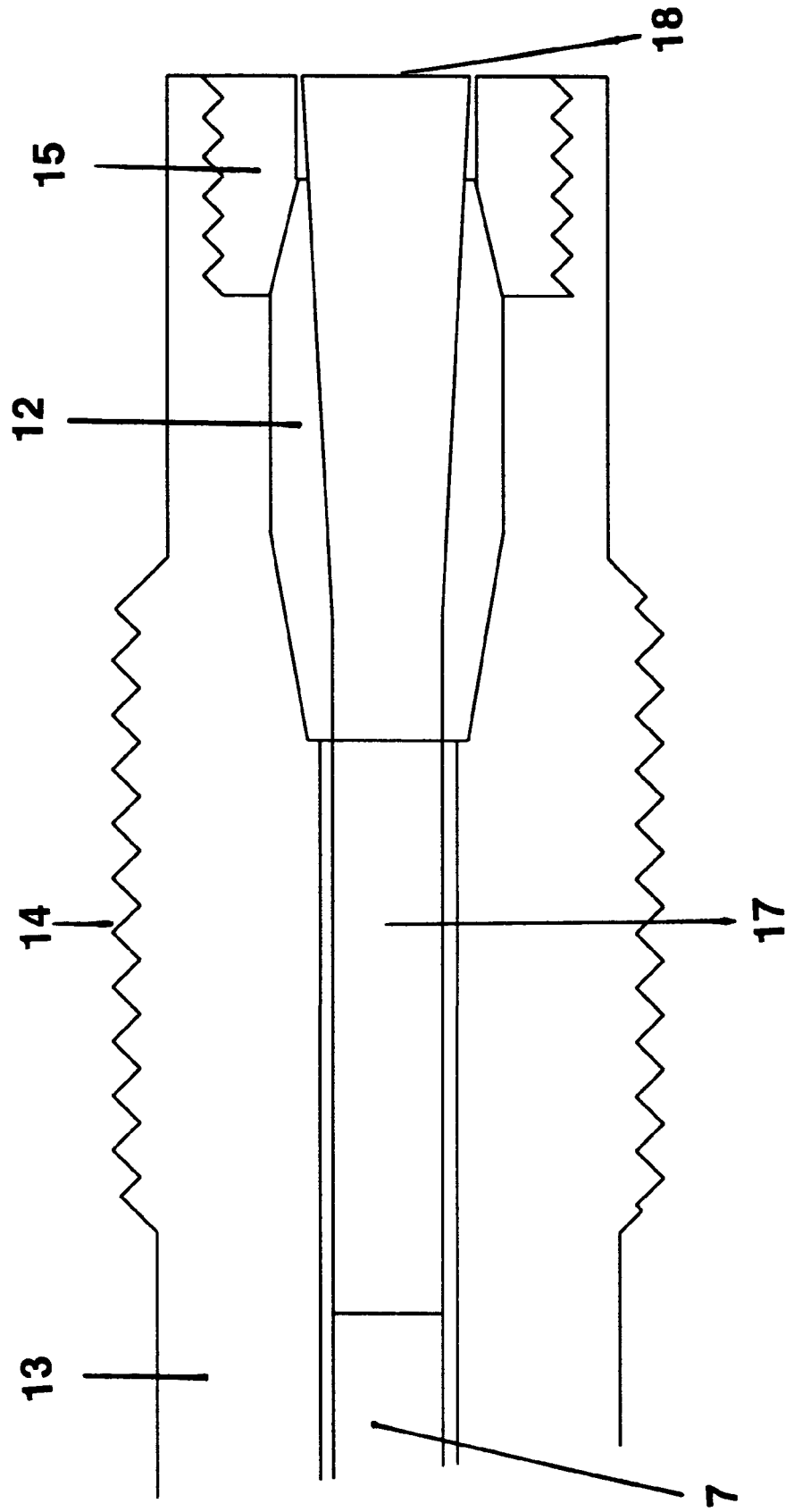
FIG. 3B is an expanded view of the end of the high-temperature reflectance sampling element.
Figure 4:
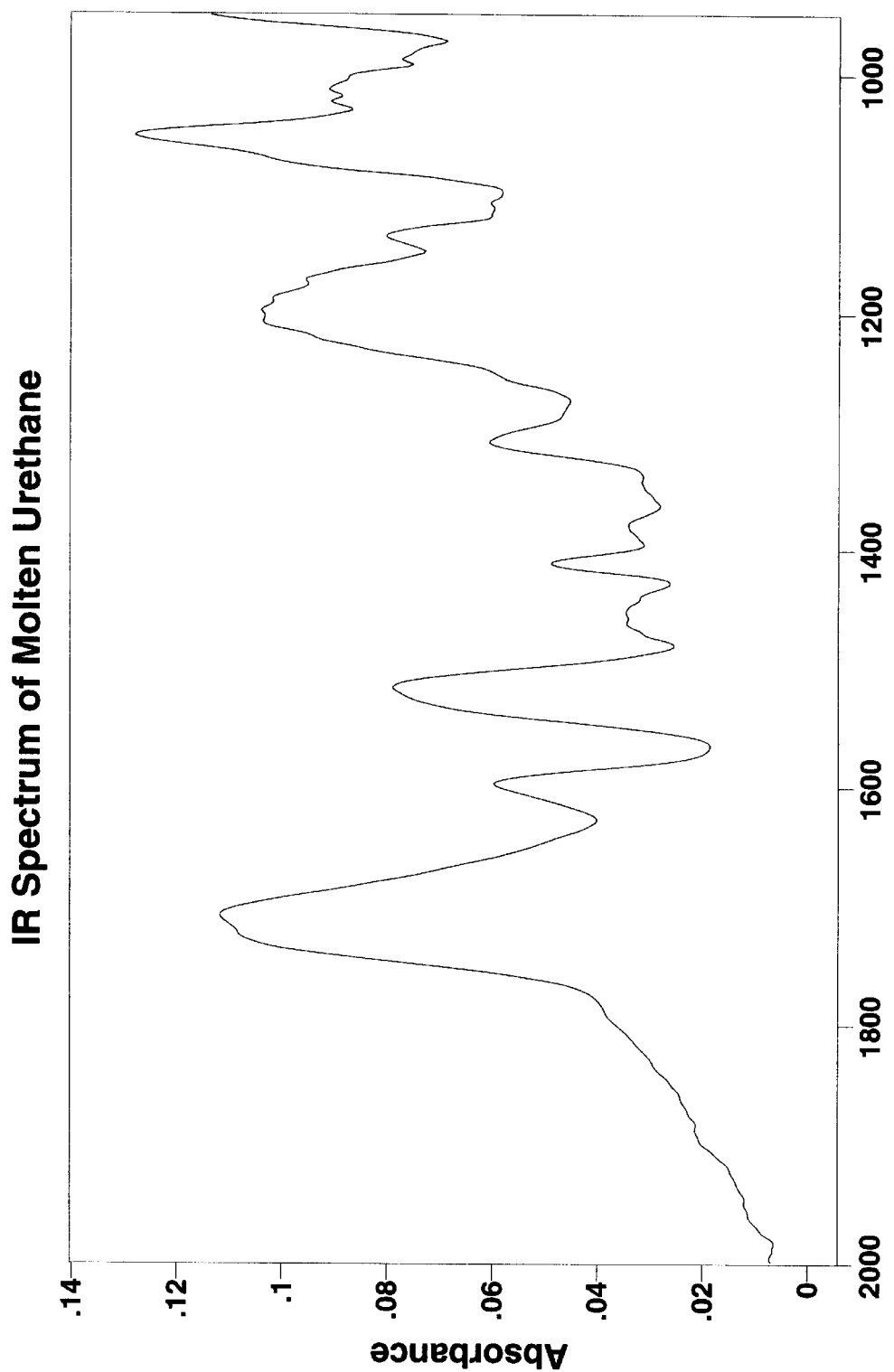
FIG. 4 is the mid-IR spectrum of a polymer melt sample.

FIG. 3B shows an expanded view of one embodiment of a reflectance sampling element. In this embodiment, the relay optic (17), which has a flat end (18) proximate to the sample, is placed next to the optically transmissive, heat-insulating member (7). In use, the IR signal travels from the relay optic to a reflective surface of the sample, from which it is reflected back into the relay optic.

EXAMPLE 1

Spectrum of a polymer melt

A probe was designed and built according to the present invention, using optical fiber cables comprising AsSeTe glass fibers. The probe was fitted with an ATR crystal made from zinc selenide and a heat-insulating, optically transparent crystal which was also made of zinc selenide. The probe head was attached to a commercial extruder by way of a Dynisco fitting so that the end of the ATR crystal protruded a short distance into the polymer melt as it flowed through the extruder. The temperature of the polymer melt during extrusion was approximately 230 deg. C. Gaseous nitrogen at room temperature was blown into the cooling inlet, and the distal ends of the input and output optical fiber cables were attached, respectively, to the external beam port of a Bruker Vector 22 FTIR spectrometer and to a mercury cadmium telluride (MCT) infrared detector fitted with specialized optics and electrically connected to the spectrometer. The spectrum shown in FIG. 3 was obtained when a molten urethane polymer was extruded, based on 64 scans at 4 scans per second, and a resolution of 4 cm$^{-1}$. The spectrum clearly shows the characteristic peaks of a urethane polymer in the region between 1000 and 2000 cm$^{-1}$, and it is clear that no deterioration of the fiber optic cables, or of the optical signal, has taken place.

While the above description contains many specific details and descriptions, these should not be taken as limiting the scope of the invention, but rather as exemplifications of preferred embodiments. Many other variations are possible, and will be apparent to those skilled in the art. The scope of the invention should be determined not by the embodiments illustrated, but by the appended claims and their legal equivalents.

What is claimed is:

1. A spectroscopic probe for attachment to a fiber-optic cable, comprising a probe body including a conduit and a sampling element which is placed inside the said conduit, characterized in that the sampling element is connected to the fiber-optic cable by means of an optically transparent, heat-insulating member which is interposed between the sampling element and the end of the fiber-optic cable, and further characterized in that means are provided for cooling the optically transparent, heat-insulating member by exposing at least part of its exterior surface to a flow of cooling fluid.

2. A spectroscopic probe according to claim 1, characterized in that the cooling fluid is gaseous nitrogen.

3. A spectroscopic probe according to claim 1, characterized in that a seal is interposed between the outside surface of the sampling element and the inside surface of the conduit.

4. A spectroscopic probe according to claim 3, characterized in that the inner surface of the seal and the outer surface of the sampling element are matchingly tapered so that the diameter is smaller at the end of the sampling element proximate to the optically transparent; heat-insulating member than at the end which is distant from the optically transparent, heat-insulating member.

5. A spectroscopic probe according to claim 1, characterized in that the optically transparent, heat-insulating member is composed of a material selected from the set consisting of zinc sulfide, zinc selenide, and arsenic-germanium-selenium-tellurium glass.

6. A spectroscopic probe according to claim 1, characterized in that the sampling element is selected from the set consisting of an ATR crystal, a transmission head, and a reflectance head.

7. A spectroscopic probe for attachment to a fiber-optic cable, comprising a probe body including a conduit and a sampling element which is placed inside the said conduit, characterized in that the sampling element is connected to the fiber-optic cable by means of an optically transparent, heat-insulating member which is interposed between the sampling element and the end of the fiber-optic cable, and further characterized in that a seal is interposed between the outside surface of the sampling element and the inside surface of the conduit, the seal and the conduit being matchingly tapered so that the diameter is smaller at the end of the sampling element proximate to the optically transparent, heat-insulating member than at the end which is distant from the optically transparent, heat-insulating member.

8. A spectroscopic probe according to claim 7, characterized in that the optically transparent, heat-insulating member is composed of a material selected from the set consisting of zinc sulfide, zinc selenide, and arsenic-germanium-selenium-tellurium glass.

9. A spectroscopic probe according to claim 7, characterized in that means are provided for cooling the optically transparent, heat-insulating member by exposing at least part of its exterior surface to a flow of cooling fluid.

10. A spectroscopic probe according to claim 9, characterized in that the cooling fluid is gaseous nitrogen.

* * * * *